US00PP32141P2

(12) United States Plant Patent
Kolster et al.

(10) Patent No.: US PP32,141 P2
(45) Date of Patent: Sep. 1, 2020

(54) ***HYDRANGEA* PLANT NAMED 'HOKOMAGREJO'**

(50) Latin Name: *Hydrangea macrophylla*
Varietal Denomination: Hokomagrejo

(71) Applicants: KOLSTER HOLDING B.V., Boskoop (NL); HORTEVE BREEDING B.V., Aalsmeer (NL)

(72) Inventors: Peter R. Kolster, Boskoop (NL); Cornelis P. Eveleens, Aalsmeer (NL)

(73) Assignees: Kolster Holding B.V., Boskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 16/602,294

(22) Filed: Sep. 6, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 6/48
See application file for complete search history.

*Primary Examiner* — Annette H Para
(74) *Attorney, Agent, or Firm* — C. A. Whealy

(57) ABSTRACT

A new and distinct cultivar of *Hydrangea* plant named 'Hokomagrejo', characterized by its upright to somewhat outwardly spreading plant habit; vigorous growth habit and moderate to rapid growth rate; freely branching habit with strong and thick sturdy stems; freely flowering habit; large mophead-type inflorescences with yellow green-colored sterile flowers with red purple-colored centers and margins; and good postproduction longevity.

2 Drawing Sheets

Figure 1:
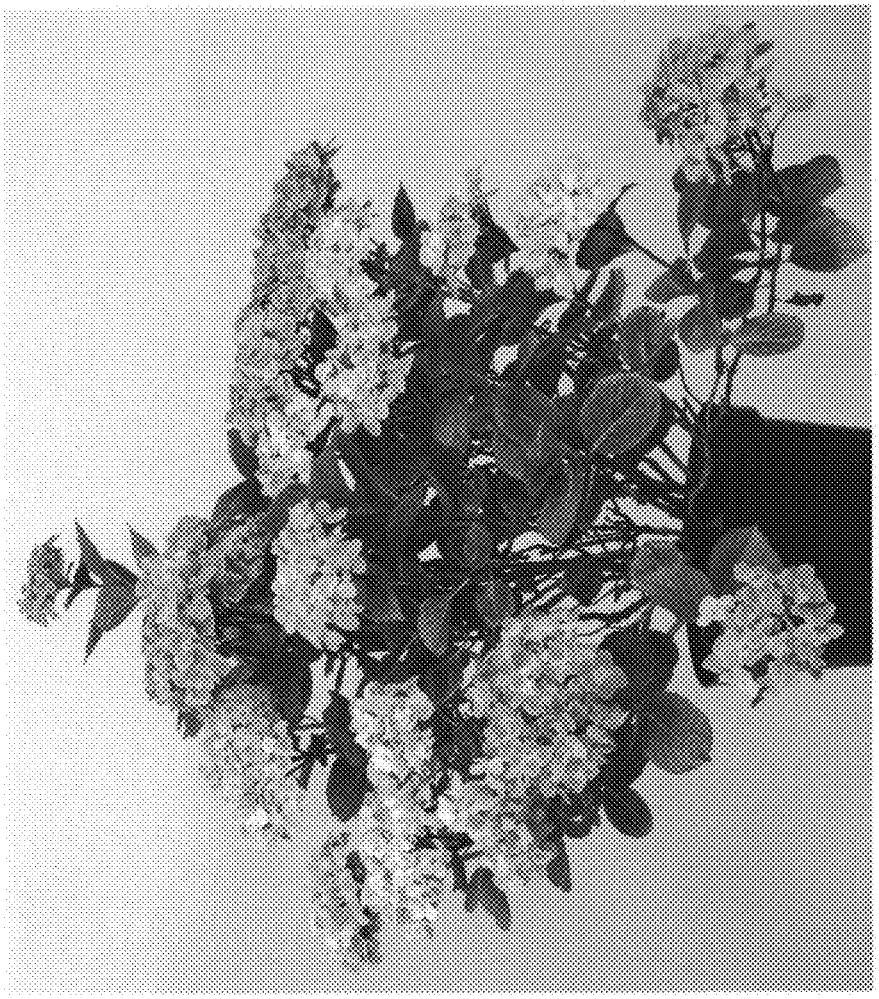

Botanical designation: *Hydrangea macrophylla.*
Cultivar denomination: 'HOKOMAGREJO'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hokomagrejo'.

The new *Hydrangea* plant is a product of a planned breeding program conducted by the Inventors in Boskoop, The Netherlands. The objective of the breeding program was to create new potted *Hydrangea* plants with large showy inflorescences with numerous attractive and unique sterile flowers and good postproduction longevity.

The new *Hydrangea* plant originated from a cross-pollination made by the Inventors on May 6, 2012 in Boskoop, The Netherlands, of *Hydrangea macrophylla* 'Green Shadow', not patented, as the female, or seed, parent with *Hydrangea macrophylla* 'Hokomasugre', not patented, as the male, or pollen, parent. The new *Hydrangea* plant was discovered and selected by the Inventors as a single flowering plant from within the progeny of the stated cross-pollination in a controlled greenhouse environment in Boskoop, The Netherlands in June, 2014.

Asexual reproduction of the new *Hydrangea* plant by vegetative terminal cuttings in a controlled environment in Boskoop, The Netherlands since August, 2014 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hokomagrejo'. These characteristics in combination distinguish 'Hokomagrejo' as a new and distinct *Hydrangea* plant:

1. Upright to somewhat outwardly spreading plant habit.
2. Vigorous growth habit and moderate to rapid growth rate.
3. Freely branching habit with strong and thick sturdy stems.
4. Freely flowering habit.
5. Large mophead-type inflorescences with yellow green-colored sterile flowers with red purple-colored centers and margins.
6. Good postproduction longevity.

Plants of the new *Hydrangea* can be compared to plants of the female parent, 'Green Shadow'. Plants of the new *Hydrangea* differ primarily from plants of 'Green Shadow' in sterile flower color as sterile flower sepals of plants of the new *Hydrangea* are yellow green in color with red purple-colored centers and margins whereas sterile flower sepals of plants of 'Green Shadow' are initially bright green in color becoming dark red in color with development.

Plants of the new *Hydrangea* can be compared to plants of the male parent, 'Hokomasugre'. Plants of the new *Hydrangea* differ primarily from plants of 'Hokomasugre' in sterile flower color as sterile flower sepals of plants of the new *Hydrangea* are yellow green in color with red purple-colored centers and margins whereas sterile flower sepals of plants of 'Hokomasugre' are green in color with white-colored centers. In addition, sterile flower sepals of plants of the new *Hydrangea* are entire whereas sterile flower sepals of 'Hokomasugre' are crenate.

Plants of the new *Hydrangea* can be compared to plants of *Hydrangea macrophylla* 'Hortmagreclo', disclosed in U.S. Plant Pat. No. 28,063. Plants of the new *Hydrangea* differ primarily from plants of 'Hortmagreclo' in sterile flower color as sterile flower sepals of plants of the new *Hydrangea* are yellow green in color with red purple-colored centers and margins whereas sterile flower sepals of plants of 'Hortmagreclo' are green in color with white-colored centers. In addition, sterile flower sepals of plants of the new *Hydrangea* are entire whereas sterile flower sepals of 'Hortmagreclo' are crenate.

Plants of the new *Hydrangea* can be compared to plants of *Hydrangea macrophylla* 'Hortmarhaso', not patented. Plants of the new *Hydrangea* differ primarily from plants of 'Hortmarhaso' in sterile flower color as sterile flower sepals of plants of the new *Hydrangea* are yellow green in color with red purple-colored centers and margins whereas sterile flower sepals of plants of 'Hortmarhaso' are green in color with white-colored centers. In addition, sterile flower sepals of plants of the new *Hydrangea* are entire whereas sterile flower sepals of 'Hortmarhaso' are crenate.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'Hokomagrejo' grown in a container.

Figure 2:
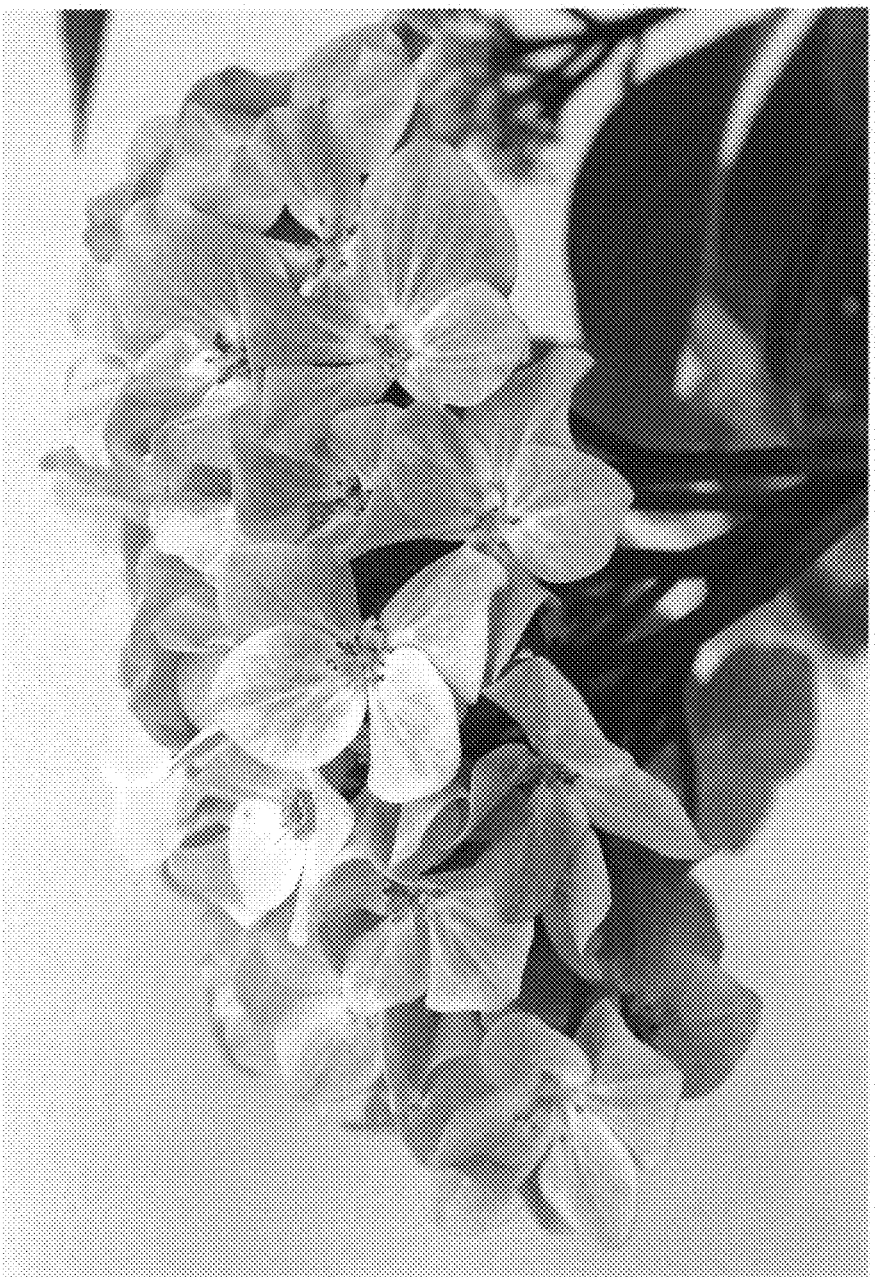

The photograph on the second sheet (FIG. 2 of 2) is a close-up view of a typical inflorescence of 'Hokomagrejo'.

DETAILED BOTANICAL DESCRIPTION

Plants used in the aforementioned photographs and in the following description were grown during the summer in 17-cm containers in a glass-covered greenhouse in Boskoop, The Netherlands and under cultural practices typical of commercial *Hydrangea* production. During the production of the plants, day temperatures ranged from 20° C. to 35° C. and night temperatures ranged from 10° C. to 22° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hokomagrejo'.

Parentage:

- *Female, or seed, parent.*—*Hydrangea macrophylla* 'Green Shadow', not patented.
- *Male, or pollen, parent.*—*Hydrangea macrophylla* 'Hokomasugre', not patented.

Propagation:

- *Type cutting.*—By vegetative terminal cuttings.
- *Time to initiate roots, summer.*—About four weeks at temperatures about 15° C. to 25° C.
- *Time to initiate roots, winter.*—About six weeks at temperatures about 15° C. to 21° C.
- *Time to produce a rooted young plant, summer.*—About 100 days at temperatures about 15° C. to 25° C.
- *Time to produce a rooted young plant, winter.*—About 140 days at temperatures about 15° C. to 21° C.
- *Root description.*—Medium in thickness, fibrous; typically creamy white in color, actual color of the roots is dependent on substrate composition, water quality, fertilizer type and formulation, substrate temperature and physiological age of roots.
- *Rooting habit.*—Moderately freely branching; medium density.

Plant description:

- *Plant and growth habit.*—Upright to somewhat outwardly spreading plant habit; overall plant shape, globular; strong and sturdy lateral branches; vigorous growth habit and moderate to rapid growth rate.
- *Plant height.*—About 69 cm.
- *Plant diameter or area of spread.*—About 88 cm.

Lateral branch description:

- *Branching habit.*—Freely branching habit about 38 lateral branches develop per plant; pinching will enhance branching.
- *Length.*—About 21.1 cm.
- *Diameter.*—About 5 mm.
- *Internode length.*—About 5.4 cm.
- *Texture.*—Smooth, glabrous; fully developed, woody.
- *Aspect.*—Varying from upright to about 60° from vertical.
- *Strength.*—Strong, sturdy.
- *Color.*—When developing: Close to 144A. Developed: Close to 144B; at the internodes, occasionally tinged with close to 183A; when woody, close to 199B to 199C.
- *Lenticels.*—Density: Medium density. Length: About 2 mm. Diameter: About 1 mm. Color: Close to N186C.

Leaf description:

- *Arrangement.*—Opposite, simple.
- *Length.*—About 9.2 cm.
- *Width.*—About 7 cm.
- *Shape.*—Broadly ovate.
- *Apex.*—Short apiculate.
- *Base.*—Short attenuate.
- *Margin.*—Serrate.
- *Texture, upper surface.*—Smooth to slightly rugose, glabrous.
- *Texture, lower surface.*—Smooth to moderately rugose, glabrous.
- *Venation pattern.*—Pinnate.
- *Color.*—Developing leaves, upper surface: Close to NN137B. Developing leaves, lower surface: Close to between 138A and 147B. Fully expanded leaves, upper surface: Close to 137B; venation, close to 146D. Fully expanded leaves, lower surface: Close to 146B; venation, close to 146D.
- *Petioles.*—Length: About 2.3 cm. Diameter: About 3.5 mm. Texture and luster, upper and lower surfaces: Smooth, glabrous; moderately glossy. Color, upper and lower surfaces: Close to 145A.

Flower description:

- *Flower type and habit.*—Showy sterile flowers and small inconspicuous fertile flowers arranged on mophead-type terminal panicles; panicles flattened globular in shape; fertile flowers face mostly upright and sterile flowers face upright to outwardly depending on their position in the inflorescence.

*Fragrance*.—None detected.

*Natural flowering season*.—Plants flower from late spring to late summer in The Netherlands.

*Flower longevity*.—Fertile flowers last about three days on the plant, fertile flowers not persistent; sterile flowers last about six weeks on the plant, sterile flowers persistent.

*Quantity of flowers*.—Freely flowering habit; about 45 fertile flowers per panicle and about 75 sterile flowers per panicle.

*Panicle height*.—About 10.9 cm.

*Panicle diameter*.—About 17 cm.

*Fertile flower buds*.—Length: About 3 mm. Diameter: About 2 mm. Shape: Ovate. Color: Close to 144A.

*Sterile flower buds*.—Length: About 1 cm. Diameter: About 1.5 cm. Shape: Cup-shaped. Color: Close to 144A.

*Fertile flower diameter*.—About 1.5 cm.

*Fertile flower depth* (*height*).—About 5 mm.

*Sterile flower diameter*.—About 4.2 cm.

*Sterile flower depth* (*height*).—About 1.6 cm.

*Petals, fertile flowers*.—Quantity and arrangement: Five in a single whorl. Length: About 7 mm. Width: About 4 mm. Shape: Ovate, slightly concave. Apex: Acute. Base: Cuneate. Margin: Entire. Texture and luster, upper and lower surfaces: Smooth, glabrous; matte. Color: When opening, upper and lower surfaces: Close to 144A. Fully opened, upper surface: Close to 144A fading towards the base to close to 150D; at the base, tinged with close to 69C; color does not change with development. Fully opened, lower surface: Close to 144A fading towards the base to close to 150D; color does not change with development.

*Petals, sterile flowers*.—Quantity and arrangement: About four, occasionally five, in a single whorl. Length: About 6 mm. Width: About 4 mm. Shape: Ovate, moderately concave. Apex: Acute. Base: Cuneate. Margin: Entire. Texture and luster, upper and lower surfaces: Smooth, glabrous; matte. Color: When opening, upper surface: Close to 145A fading towards the base to close to 145B; at the base, close to 63B. When opening, lower surface: Close to 61D. Fully opened, upper surface: Close to 63C; color does not change with development. Fully opened, lower surface: Close to 63C to 63D; color does not change with development.

*Sepals, fertile flowers*.—Quantity and arrangement: About five in a single whorl. Length: About 1 mm. Width: About 2 mm. Shape: Deltoid. Apex: Broadly acute. Base: Broadly cuneate. Margin: Entire. Texture and luster, upper and lower surfaces: Smooth, glabrous; matte. Color: When opening and fully opened, upper surface: Close to 145C; color does not change with development. When opening and fully opened, lower surface: Close to 145C; color does not change with development.

*Sepals, sterile flowers*.—Quantity and arrangement: Four, occasionally five, in a single whorl. Length: About 2.3 cm. Width: About 2.2 cm. Shape: Broadly ovate to nearly deltoid. Apex: Obtuse to bluntly and broadly acute. Base: Broadly cuneate. Margin: Entire, slightly undulate. Texture and luster, upper and lower surfaces: Smooth, glabrous; matte. Color: When opening, upper surface: Close to 145A fading towards the base to close to 145B; at the base, close to 63C. When opening, lower surface: Close to 145B; at the base, close to 63D. Fully opened, upper surface: Close to 145A; distal margins tinged with close to 63B; at the base, close to 64D; with development, main color becoming closer to 144A to 144B with distal margins, closer to 59D and base tinged with close to 64D. Fully opened, lower surface: Close to 145B; at the base, close to 63D; with development, base color becoming closer to 63C to 63D.

*Pedicels, fertile flowers*.—Length: About 8 mm. Diameter: About 1 mm. Strength: Moderately strong. Aspect: About 40° from vertical. Texture and luster: Moderately pubescent; matte. Color: Close to 182C to 182D.

*Pedicels, sterile flowers*.—Length: About 2.2 cm. Diameter: About 1.5 mm. Strength: Moderately strong. Aspect: About 30° from peduncle axis. Texture and luster: Moderately pubescent; matte. Color: Close to 64D.

*Reproductive organs, fertile flowers*.—Stamens: Quantity per flower: About ten. Filament length: About 3 mm. Filament color: Close to 75A. Anther length: About 1 mm. Anther shape: Broadly oblong. Anther color: Close to 158B. Pollen amount: Scarce. Pollen color: Close to 155D. Pistils: Pistil quantity per flower: About three, occasionally two. Pistil length: About 1.25 mm. Stigma shape: Club-shaped. Stigma color: Close to 64A. Style length: About 1 mm. Style color: Close to 64A. Ovary color: Close to 70D.

*Reproductive organs, sterile flowers*.—Stamens: Quantity per flower: About ten. Filament length: About 3 mm. Filament color: Close to 75A. Anther length: About 1 mm. Anther shape: Broadly oblong. Anther color: Close to 158B. Pollen amount: Scarce. Pollen color: Close to 155D. Pistils: Pistil quantity per flower: About three, occasionally two. Pistil length: About 1.25 mm. Stigma shape: Club-shaped. Stigma color: Close to 64A. Style length: About 1 mm. Style color: Close to 70C. Ovary color: Close to 70D.

*Seeds*.—To date, seed development has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been observed to tolerate temperatures ranging from −20° C. to 35° C. and are suitable for USDA Hardiness Zones 5 to 9.

It is claimed:

1. A new and distinct *Hydrangea* plant named 'Hokomagrejo' as illustrated and described.

* * * * *